United States Patent [19]

Pletka et al.

[11] 4,072,701
[45] Feb. 7, 1978

[54] PROCESS FOR THE PRODUCTION OF SULFUR CONTAINING ORGANOSILICON COMPOUNDS

[75] Inventors: Hans-Dieter Pletka, Hanau; Rudolf Michel, Freigericht, both of Germany

[73] Assignee: Deutsche Gold- und Silber-Scheideanstalt vormals Roessler, Frankfurt, Germany

[21] Appl. No.: 730,726

[22] Filed: Sept. 24, 1976

[30] Foreign Application Priority Data

Sept. 24, 1975 Germany ............................ 2542534

[51] Int. Cl.$^2$ .............................................. C07F 7/18
[52] U.S. Cl. ...................... 260/448.8 R; 260/448.2 W
[58] Field of Search ................................. 260/448.8 R

[56] References Cited

U.S. PATENT DOCUMENTS

| | | | |
|---|---|---|---|
| 3,530,160 | 9/1970 | Gardner et al. .......... | 260/448.8 R X |
| 3,842,111 | 10/1974 | Meyer-Simon et al. .... | 260/448.8 R X |
| 3,873,489 | 3/1975 | Thurn et al. .............. | 260/448.8 R X |
| 3,946,059 | 3/1976 | Janssen et al. ............ | 260/448.8 R X |

Primary Examiner—Paul F. Shaver
Attorney, Agent, or Firm—Cushman, Darby & Cushman

[57] ABSTRACT

There is provided a process for the production of sulfur containing organosilicon compounds of the formula (I) Z—Alk—S$_x$—Alk-Z, where Z is the grouping:

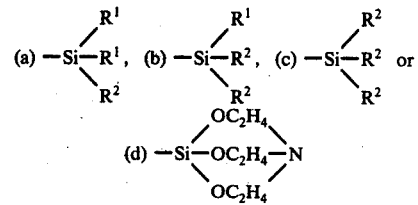

in which $R^1$ is an alkyl group having 1 to 8 carbon atoms, a cycloalkyl group with 5 to 8 carbon atoms, the benzyl group, phenyl or phenyl substituted with at least one methyl, ethyl or chloro group and $R^2$ is alkoxy of 1 to 8 carbon atoms, methoxyethoxy, cycloalkoxy with 5 to 8 carbon atoms, phenoxy or benzyloxy, Alk is divalent saturated hydrocarbon group having 1 to 10 carbon atoms or such a group interrupted once or twice by —O—, —S— or —NH— and $x$ is a number from 2.0 to 6.0 comprising reacting a compound of the formula (II) Y—Alk—Hal, where Y is:

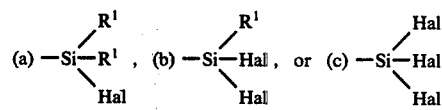

where Hal is fluorine, chlorine, bromine or iodine with at least one compound of the formula $R^3OH$ in which $R^3$ is alkyl of 1 to 8 carbon atoms, methoxyethyl, cycloalkyl with 5 to 8 carbon atoms, phenyl or benzyl or in the case of forming (d) reacting a tris alkoxysilane with triethanolamine to form the corresponding silatrane and with a hydrosulfide of the formula (III) MeSH, in which Me is ammonium, an alkali metal atom or an equivalent of an alkaline earth metal and with sulfur, preferably in the presence of at least one organic solvent, separating from the halide formed, and removing the organic solvent.

18 Claims, No Drawings

PROCESS FOR THE PRODUCTION OF SULFUR CONTAINING ORGANOSILICON COMPOUNDS

The present invention is directed to the production of sulfur containing organosilicon compounds by a new process which can be carried out in a simple, safe and problem free manner from readily available starting materials and with a practically quantitative progress of the reaction.

The process of the invention produces organosilicon compounds of the formula (I) Z — Alk — $S_x$ — Alk — Z, in which Z is the group:

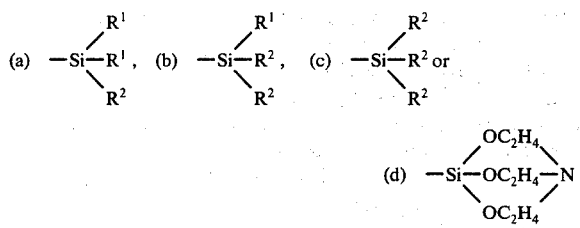

in which $R^1$ is a straight or branched chain alkyl group of 1 to 8 carbon atoms, a cycloalkyl group with 5 to 8 carbon atoms, the benzyl group, phenyl or phenyl substituted with one or more, e.g., 2 or 3, methyl, ethyl or chloro groups, $R^2$ is an alkoxy group having a straight or branched carbon chain with 1 to 8 carbon atoms, the methoxyethoxy group, a cycloalkoxy group with 5 to 8 carbon atoms, the phenoxy group or the benzyloxy group, wherein $R^1$ and $R^2$ can be the same or different, Alk is a divalent saturated hydrocarbon group, e.g., alkylene, with 1 to 10 carbon atoms which can be in a straight or branched carbon chain which can be interrupted once or twice by —O—, —S— or —NH—, and $x$ is a number from 2.0 to 6.0. The process comprises reacting a compound of the formula (II) Y — Alk — Hal, in which Y is the group:

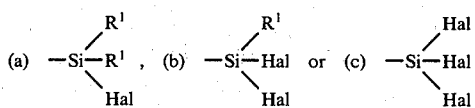

in which $R^1$ is as defined above and Hal is a fluorine, chlorine, bromine or iodine atom (i.e., halogen of atomic weight 9 to 127) with at least one compound of the formula $R^3OH$ in which $R^3$ is an alkyl group with a straight or branched carbon chain with 1 to 8 carbon atoms, the methoxyethyl group, a cycloalkyl group with 5 to 8 carbon atoms, the phenyl group or the benzyl group and in a given case in the case of the tris alkoxysilane reacting this in known manner with triethanolamine using a known transesterification catalyst to form the corresponding silatrane

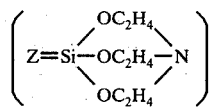

and further reacting with
a hydrosulfide of the formula (III) MeSH in which Me is an alkali metal atom, e.g., sodium, potassium, rubidium or cesium, ammonium or one equivalent of an alkaline earth metal, e.g., magnesium, calcium, barium or strontium or zinc and reacting with sulfur, preferably in the presence of at least one organic solvent, separating from the halide formed and then removing the organic solvent (if used). The amount of sulfur should be sufficient together with the sulfur in MeSH to satisfy the value of $x$ in formula (I).

The preferred compounds of the above mentioned formula III are NaSH, KSH, CsSH and (NH$_4$)SH.

The elemental sulfur is advantageously added in finely divided form, for example as sulfur powder. To accelerate the running of the reaction the hydrosulfide is also preferably added in powder form. The reaction generally begins even at room temperature and it can be continued further by itself as an exothermic reaction. Suitably to shorten the total reaction time the operation is carried out at elevated or increasing temperature which can rise to the boiling point of the solvent or solvent mixture used. Especially advantageous is the use of an inert organic solvent of not too high boiling point, which is capable of dissolving the reactants wholly or in part. Such solvents include, for example, dioxane, dimethyl formamide, tetrahydrofuran and particularly acetone as well as preferably alcohols, especially primary lower aliphatic alcohols or cycloaliphatic alcohols, e.g., methyl alcohol, isopropyl alcohol, and n-butyl alcohol, cyclohexanol and cyclopentanol.

Furthermore, it is advantageous to carry out the reaction while excluding air and/or water (moisture) to suppress the formation of byproducts or to substantially avoid their formation. One can operate for example under a dry inert gas such as nitrogen or under a noble gas, e.g., argon, neon or helium. It can be especially suitable if there is added or used the hydrogen sulfide formed by reaction of elemental sulfur with MeSH. It can also be suitable to carry the reaction under reduced pressure or slightly elevated pressure.

It can be particularly desirable to so proceed in carrying out the process of the invention that a compound of general formula II is first reacted with a compound of the formula $R^3OH$, preferably an alcohol of the series of primary lower aliphatic alcohols, specifically lower alkanols, and then drive out the hydrogen halide formed. Then there is added a further amount of the compound $R^3OH$, thus preferably an alcohol, or there is added an organic solvent as well as sulfur. As a solvent for this purpose there should be employed advantageously an organic compound which excludes undesired transesterification on the silicon atom.

The reaction of the invention is carried out practically quantitatively according to the following equations:

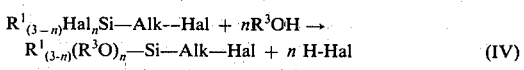

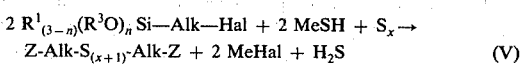

In both equations (IV) and (V) the designations are the same as set forth above and $n$ is 1 to 3.

Toward the end of the reaction the evolution of the hydrogen sulfide diminishes. A certain past reactions time can be advantageous. After ending the reaction, the reaction mixture in a given case is cooled, filtered off from the separated salt and then the organic solvent advantageously removed by distillation, if desired under reduced pressure. The organosilicon compound formed as the end product cannot be distilled under conventional conditions without decomposition. Therefore they are collected in the sump of the distillation column and in most cases can be used directly for the desired purpose without purification. For example, they can be added as valuable adhesive aids or reinforcing additives in rubber compositions containing silica or silicate fillers. However, they also make valuable intermediate products.

The poly or oligosulfidic silanes of formula I for the most part are known (see Belgian Pat. No. 787,691, as well as related Meyer-Simon U.S. Pat. No. 3,842,111 as well as Thurn Pat. No. 3,873,489. The entire disclosures of Meyer-Simon and Thurn are hereby incorporated by reference and relied upon.) However, the compounds are made by other processes than that of the present invention. Also it has already been proposed to produce these silanes by direct reaction of mercaptoalkylsilanes with sulfur. In Janssen German Offenlegungsschrift 2 360 471 there is described a process in which the corresponding polysulfides are obtained by building elemental sulfur into organosilylalkyl disulfides. However, this process has several strong disadvantages compared to the process of the present invention. While in the process of the invention one starts with the easily available haloalkylsilanes and obtained the polysulfides in one reaction step, according to the known process the mercaptoalkylsilanes must be first produced from these haloalkylsilanes and then there is produced by oxidation in a further reaction step the necessary disulfides employed as starting materials. Furthermore, the reaction times of 15 to 50 hours at reaction temperatures around 150° C are a further disadvantage. In contrast to these known syntheses the process of the invention is surprisingly simple. The expenditure for apparatus and time in carrying out the new process is very small and the running of the reaction is quantitative. Therewith the process is also very economical, the starting materials are chiefly easily available.

Preferred silanes according to formula I are: the bis-[trialkoxysilyl-alkyl-(1)]-polysulfides such as the bis-trimethoxy-, -triethoxy-, -tri-(methylethoxy)-, tripropoxy-, -tributoxy-, etc., up to the -trioctyloxysilylmethyl]-polysulfides; furthermore the bis-[2-trimethoxy-, -triethoxy-, -tri-(methylethoxy)-, -tripropoxy-, -tributoxy-, etc., up to the trioctyloxysilyl-ethyl]-polysulfides namely the di-, tri-, tetra-, penta- and hexasulfide, preferably the bis-[3-trimethoxy-, -triethoxy-, -tri-(methylethoxy)-, -tripropoxy-, tributoxy-, etc., up to the -trioctyloxysilylpropyl]-polysulfides, again the di-, tri-, tetra-, etc., up to the hexasulfides; furthermore the corresponding bis-[3-trialkoxysilyl-isobutyl]-polysulfides, the corresponding bis-[4-trialkoxysilylbutyl]-polysulfides, etc., up to the bis-[10-trialkoxysilyldecyl]-polysulfides. Of those selected there are preferred the relatively simple organosilanes of formula I such as the bis-[3-trimethoxy-, -triethoxy- and -tripropoxysilylpropyl]-polysulfides, preferably the tri-, tetra- and pentasulfide. Examples of silanes of formula I produced according to the invention include bis-(3-trimethoxysilylpropyl)-trisulfide, bis-(3-triethoxysilylpropyl)-tetrasulfide, bis-(3-trimethoxysilylpropyl)-tetrasulfide, bis-(2-triethoxysilylethyl)-tetrasulfide, bis-(3-trimethoxysilylpropyl)-disulfide, bis-(3-triethoxysilylpropyl)-trisulfide, bis-(3-tributoxysilylpropyl)-pentasulfide, bis-(3-trimethoxysilylpropyl)-hexasulfide, bis-(3-trioctoxysilylpropyl)-tetrasulfide, bis-(3-trihexoxysilylpropyl)-pentasulfide, bis-[3-tris-(2-ethylhexoxy-silylpropyl]-tetrasulfide, bis-tri-(3-isooctoxysilylpropyl)-tetrasulfide, bis-(tris-t-butoxysilylmethyl)-trisulfide, bis-(2-methoxydiethoxysilylethyl)-tetrasulfide, bis-(2-tri-i-propoxysilylethyl)-pentasulfide, bis-(3-tricyclohexoxysilylpropyl)-tetrasulfide, bis-(3-tricyclopentoxysilylpropyl)-trisulfide, bis-[3-tris-(4-methylcyclohexoxy)silylethyl]-tetrasulfide, bis-(dimethoxyphenoxysilylmethyl)-tetrasulfide, bis-(3-dimethoxymethylsilylpropyl)-di-, -tri- and tetrasulfides, bis-(3-dimethoxyethylsilylpropyl)-di-, -tri- and -tetrasulfides, bis-(3-dimethoxymethylsilylpropyl)-di-, -tri- and -tetrasulfides, bis-(3-diethoxyethylsilylpropyl)-di-, -tri- and -tetrasulfides, bis-(3-methoxydimethylsilylpropyl)-di-, -tri- and -tetrasulfides, bis-(3-ethoxydimethylsilylpropyl)-di-, -tri- and -tetrasulfides, bis-(3-diethylethoxysilylpropyl)-tetrasulfide, bis-(2-dimethoxymethylsilylethyl)-disulfide, bis-(3-di-i-propoxymethylsilylpropyl)-di-, -tri- and -tetrasulfides, bis-(3-di-i-propoxyethylsilylpropyl)-di, -tri- , and -tetrasulfides, bis-(4-diethoxyethylsilylbutyl)-trisulfides, bis-(5-triethoxysilylpentyl)-pentasulfide, bis-(6-phenyldimethoxysilylhexyl)-tetrasulfides, bis-(8-triethoxysilyloctyl)-hexasulfide, bis-[9-ethylbis-(methoxyethoxy)-silyl-nonyl]-tetrasulfide, 3-methoxyethoxypropoxysilylpropyl-3-dimethoxyethoxysilylpropyltetrasulfide, bis-(10-methyl-dimethoxysilyldecyl)-pentasulfide, bis-(2-dimethoxyphenylsilylethyl)trisulfide, bis-(3-methylbutylethoxysilylpropyl) tetrasulfide, bis-(2-ethyldiethoxysilyl-i-propyl)-tetrasulfide, bis-(3-silatranopropyl)-di-, -tri- and -tetra-, -penta- and -hexasulfide, bis (2-silatranoethyl)-di-, -tri- and -tetrasulfide, bis-(2-silatrano-i-propyl)-di-, -tri- and -tetrasulfide as well as, for example, bis-(3-silatrano-i-butyl)-di-, -tri- and -tetrasulfide.

There are also included within the invention the preparation of any of the other compounds within Formula I disclosed in Meyer-Simon U.S. Pat. No. 3,842,111 and Thurn U.S. Pat. No. 3,873,489. Other compounds which can be mentioned include bis(3-triscyclooctoxysilylpropyl) tetrasulfide, bis(3-triphenoxysilylpropyl) trisulfide, bis(2-diphenoxy-p-tolyloxysilylethyl) tetrasulfide, bis(3-tri-p-tolyoxysililpropyl) pentasulfide, bis(3-dimethoxy-p-ethylphenoxysilylpropyl) tetrasulfide, bis(3-tris 3',4'-dimethyl-phenoxysilylpropyl) tetrasulfide, bis(4-tris-p-chlorophenoxysilylbutyl) trisulfide, bis(3-tris 4',6'-dichlorophenoxysilylpropyl) tetrasulfide, bis(3-dimethoxy-p-chlorophenylsilylpropyl) tetrasulfide, bis(3-diethoxy-4',5'-dichlorophenylsilylpropyl) trisulfide, bis(3-dimethoxy-3',4'-dimethylphenylsilylpropyl) trisulfide, bis(3-dipropoxydiphenylsilylpropyl) tetrasulfide, bis(2-diethoxy-p-tolylsilylethyl) tetrasulfide, bis(3-dipropoxybenzylsilylpropyl) tetrasulfide.

In formulae I and II Alk can be methylene as well as more preferably ethylene, i-propylene, n-propylene, i-butylene or n-butylene, but it can also be n-pentylene, 2-methylbutylene, 3-methylbutylene, n-hexylene, 2-methylpentylene, 3-methylpentylene, 2,2-dimethylbutylene, 2,3-dimethylbutylene, n- and i-heptylene, octylene, nonylene or decylene. Alk also can have the following meanings: —$CH_2$—S—$CH_2$—; —$CH_2$—O—$CH_2$—; —$CH_2$—NH—$CH_2$—; —$CH_2$—S—$CH_2CH_2$—; —$CH_2$—O—$CH_2CH_2$—; —$CH_2$—NH—$CH_2CH_2$—; —$CH_2CH_2$—S—$CH_2CH_2$—; $CH_2CH_2$—O—$CH_2CH_2$—; —$CH_2CH_2$—NH—$CH_2CH_2$—; —$CH_2$—S—$CH_2$—S—$CH_2$—; —$CH_2$—O—$CH_2$—O—$CH_2$—; —$CH_2$—NH—$CH_2$—NH—$CH_2$—; —$CH_2$—S—$CH_2CH_2$—S—$CH_2$—; —$CH_2$—O—$CH_2CH_2$—O—$CH_2$—; —$CH_2$—NH—$CH_2CH_2$—NH—$CH_2$—; —$CH_2CH_2$—S—$CH_2$—S—$CH_2CH_2$—; —$CH_2CH_2$—O—$CH_2$—O—$CH_2CH_2$—;

—CH₂CH₂—NH—CH₂—NH—CH₂CH₂; —CH₂CH₂—S—CH₂CH₂—S—CH₂CH₂—; —CH₂CH₂—O—CH₂CH₂—O—CH₂CH₂; —CH₂CH₂—NH—CH₂CH₂—NH—CH₂CH₂—; —(CH₂)₃—S—(CH₂)₃—S—(CH₂)₃; —(CH₂)₃/—; —O—(CH₂)₃O—(CH₂)₃—; —(CH₂)₃—NH—(CH₂)₃—NH—(CH₂)₃—; —CH₂CH(CH₃)—O—CH₂CH(CH₃)—O—CH₃CH(CH₃)—; —(CH₂)₄—NH—(CH₂)₄—; —(CH₂)₄—O(CH₂)₄—; —(CH₂)₂CH(CH₃)—S—CH(CH₃)(CH₂)₂—; —(CH₂)₅—O(CH₂)₅—; —(CH₂)₅—S—(CH₂)₅—; —(CH₂)₅—NH—(CH₂)₅—.

In formula II Hal (including the meaning of Hal in the Y group) means a halogen atom, especially fluorine, chlorine or bromine, preferably chlorine. Halosilanes of formula II include, for example, chlormethyldimethylchlorsilane, 2-chlorethylethyldichlorsilane, 2-bromethyl-i-propyldibromsilane, 2-chlorethyltrichlorsilane, 3-chlorpropyltrichlorsilane, 3-chlorpropyldiethylchlorsilane, 3-chlorpropylcyclohexyldichlorsilane, 6-chlorhexylphenyldichlorsilane, 8-bromoctylbenzyldibromsilane, 3-brompropyltribromsilane, 9-chlornonyl-p-chlorphenyl-dichlorsilane, 7-chlorheptyl-p-ethylphenyldichlorsilane, 3-chlorpropylmethyethylchlorsilane.

There can be employed compounds of formula II such as 3-chlorpropyl trichlorosilane, 2-chlorethoxyethyl ethyl dichlorosilane, 2-chlorethoxyethoxyethyl methyl dichlorosilane, chloromethylthiomethyl propyl dichlorosilane, chloromethylazamethyl butyl dichlorosilane, chloromethoxyethoxymethyl methyl dichlorosilane, chloroethoxyethoxyethyl diethyl chlorosilane.

The compounds of the formula R³OH which are provided for the reaction with the compound of formula II are phenols or more preferably alcohols with an alcoholic hydroxyl group. The radical R³ is preferably an alkyl group with a straight or branched carbon chain. Thus R³OH can be methyl alcohol, ethyl alcohol, n-propyl alcohol, isopropyl alcohol, isobutyl alcohol, n-butyl alcohol, n-amyl alcohol, 2-methylbutyl alcohol, 3-methylbutyl alcohol, n-hexyl alcohol, n-octyl alcohol, isooctyl alcohol, methoxyethyl alcohol, cyclopentyl alcohol, cyclohexyl alcohol, cyclooctanol, 2-methylcyclopentyl alcohol, 3-methylcyclopentyl alcohol, 2-methylcyclohexyl alcohol, 2-ethylcyclohexyl alcohol, 3-ethylcyclohexyl alcohol, 4-ethylcyclohexyl alcohol, cycloheptyl alcohol, phenol or benzyl alcohol. Preferably R³OH is methyl alcohol, ethyl alcohol or isopropyl alcohol.

In formula III Me means particularly the ammonium group, sodium, potassium, an equivalent of the metals magnesium, calcium, strontium, barium or zinc. In carrying out the process of the invention there are preferably used potassium hydrosulfide, sodium hydrosulfide or ammonium hydrosulfide as compounds of formula III. They are preferably added in the most finely divided form, for example, as a powder.

To carry out the first step of the new process the equivalent ratio in amount of halosilane based on the reactive halogen atoms attached to the silicon atom to R³OH is preferably kept at a maximum of 1:1. To illustrate a compound of the formula

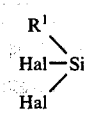

Alk Hal has two equivalents of reactive halogen attached to silicon. Preferably there is used an excess of the R³OH reactant up to four times, preferably up to 1.5 times, than required for the reaction. Thus, there can be used, for example, a 5 to 400% excess of R³OH per equivalent of halogen in the halosilane. After driving out the hydrogen halide there is added to this mixture the solvent and in a suitable manner the entire amount of sulfur powder. Then or later there is begun the stirring of the mixture and there is added the hydrosulfide in one to three portions, according to the hydrogen halide content of the oxysilane formed (within the term oxysilane there should be understood as within the space of this invention all possible reaction products of compounds of formula II with R³OH). If the oxysilane becomes free of hydrogen halide a red coloration occurs in the reaction solution. The mixture increases in temperature by itself through the exothermic nature of the reaction. However, the course of the reaction can be accelerated through heating. Generally the mixture is allowed to further react for an hour under reflux, but this is not an essential feature of the process. Then the precipitated halide salt is filtered off and the further working up is carried out in customary manner.

The new process has, among others, the advantage that the reaction sequence is carried out as a single vessel reaction. The development of hydrogen sulfide can also be controlled through regulation of the temperature. Also the hydrogen sulfide can be added to the mixture via a simple gas tight container.

However, the reactants can be brought together in other sequences. Thus according to the invention, one can so proceed that the oxysilane is added either after its isolation or in solution to the mixture of sulfur powder and hydrosulfide present in the solvent.

If it is desired to produce a silatrane advantageously one starts from a trialkoxysilane, for example, from trimethoxysilylpropyl chloride or triethoxysilylpropyl chloride and reacts it in known manner with triethanolamine, suitably using a known transesterification catalyst. Subsequently the further reaction with sulfur and hydrosulfide is carried out in the manner described above. The reaction temperature suitably is above room temperature (20° C) up to the boiling point of the solvent or mixture of solents. Higher and lower temperatures, however, are not excluded.

As transesterification catalysts there can be used, for example, in addition to KOH, NaOH and tetra lower alkyl titanates, e.g., tetra-isopropyl titanate, or any which are described in "Chemie-Lexikon" of H. Rompp, Vol. IV, page 6767 (6th edition Franckh'sche Verlagshandlurg, Stuttgart, Germany) and in "Methoden der organischen Chemie" of Houben-Weyl, Vol. 412, pages 9 and 127 (4th edition, Georg Thieme Verlag, Stuttgart, Germany, 1955).

An example of a silatrane which can be produced in advantageous manner by this process is:

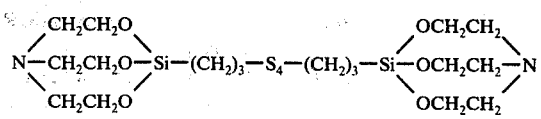

Bis-1,10(bicyclo[3,3,3]-1aza-5-sila-4,6,11-trioxaundecyl)-4,5,6,7-tetrathiadecane.

Silatrane group containing compounds of other structures which can be produced according to the process of the invention are described, for example, in the works of L. R. Garsen and L. K. Kerchner in "Journal of Pharmaceutical Sciences", Vol. 60 (1971), pages 1113 et seq., particularly page 1118 and of Voronkov et al. in Zh. Obshch. Khim., Vol. 45 (107) 1975, 7, 1649.

EXAMPLES 2 to 18

In the same way as in Example 1, additional organosilanes were produced employing the starting materials and with the analyses collected in Table 1.

TABLE 1

| STARTING MATERIALS | | | | | COMPOUND PRODUCED | | | | |
|---|---|---|---|---|---|---|---|---|---|
| | Alcohol | | | | | Analysis in Weight % | | | |
| | as | as | Sul- | | | Upper Value: | Calculated | | |
| Halosilane | reactant | solvent | fur | NaSH | | Lower Value: | Found | | |
| (amount in grams) | (g) | (g) | (g) | (g) | FORMULA | C | H | Si | S. |
| $Cl_3Si(CH_2)_3Cl/2120$ | 1450 Ethanol | 4000 | 320 | 560 | $[(C_2H_5O)_3Si(CH_2)_3]_2S_3$ | 43.85 / 43.27 | 8.13 / 8.04 | 10.81 / 10.80 | 18.91 / 18.43 |
| $Cl_3Si(CH_2)_3Cl/2120$ | 1450 Ethanol | 4000 | 180 | 560 | $[(C_2H_5O)_3Si(CH_2)_3]_2S_2$ | 45.54 / 45.30 | 8.91 / 8.72 | 11.83 / 11.61 | 13.48 / 13.97 |
| $Cl_3Si(CH_2)_3Cl/2120$ | 1000 Methanol | 4000 | 480 | 560 | $[(CH_3O)_3Si(CH_2)_3]_2S_4$ | 31.70 / 31.65 | 6.60 / 6.68 | 12.34 / 12.56 | 28.21 / 27.44 |
| $Cl_3Si(CH_2)_3Cl/2120$ | 1000 Methanol | 4000 | 320 | 560 | $[(CH_3O)_3Si(CH_2)_3]_2S_3$ | 34.12 / 34.29 | 7.11 / 7.19 | 13.29 / 13.16 | 22.76 / 23.03 |
| $Cl_3Si(CH_2)_3Cl/2120$ | 1000 Methanol | 4000 | 180 | 560 | $[(CH_3O)_3Si(CH_2)_3]_2S_2$ | 36.90 / 36.24 | 7.68 / 7.53 | 14.37 / 14.03 | 16.42 / 16.83 |
| $Cl_3Si(CH_2)_2Cl/1981$ | 1450 Ethanol | 4000 | 480 | 560 | $[(C_2H_5O)_3Si(CH_2)_2]_2S_4$ | 37.62 / 36.90 | 7.49 / 7.12 | 11.00 / 10.67 | 25.11 / 25.88 |
| $Cl_3Si(CH_2)_2Cl/1981$ | 1450 Ethanol | 4000 | 320 | 560 | $[(C_2H_5O)_3Si(CH_2)_2]_2S_3$ | 40.13 / 39.78 | 7.99 / 7.73 | 11.73 / 11.92 | 20.09 / 20.36 |
| $Cl_3Si(CH_2)_3Cl/1981$ | 1450 Ethanol | 4000 | 180 | 560 | $[(C_2H_5O)_3Si(CH_2)_2]_2S_2$ | 43.01 / 42.54 | 8.57 / 8.39 | 12.56 / 12.34 | 14.35 / 14.82 |
| $Cl_3Si(CH_2)_2Cl/1981$ | 1000 Methanol | 4000 | 480 | 560 | $[(CH_3O)_3Si(CH_2)_2]_2S_4$ | 28.14 / 27.76 | 6.14 / 6.09 | 13.16 / 13.25 | 30.05 / 29.34 |
| $Cl_3Si(CH_2)_2Cl/1981$ | 1000 Methanol | 4000 | 320 | 560 | $[(CH_3O)_3Si(CH_2)_2]_2S_3$ | 30.43 / 30.40 | 6.64 / 6.53 | 14.23 / 14.39 | 24.37 / 23.98 |
| $Cl_3Si(CH_2)_2Cl/1981$ | 1000 Methanol | 4000 | 180 | 560 | $[(CH_3O)_3Si(CH_2)_2]_2S_2$ | 33.12 / 32.87 | 7.23 / 7.16 | 15.49 / 15.55 | 17.68 / 17.93 |
| $Cl_3Si(CH_2)_3Cl/2120$ | 1900 i-Propanol | 4000 | 480 | 560 | $[(i-C_3H_7O)_3Si(CH_2)_3]_2S_4$ | 46.26 / 45.83 | 8.73 / 8.63 | 9.01 / 9.27 | 20.58 / 20.17 |
| $Cl_3Si(CH_2)_3Cl/2120$ | 1900 i-Propanol | 4000 | 320 | 560 | $[(i-C_3H_7O)_3Si(CH_2)_3]_2S_3$ | 48.77 / 48.42 | 9.21 / 9.12 | 9.50 / 9.57 | 16.72 / 16.41 |
| $Cl_3Si(CH_2)_3Cl/2120$ | 1900 i-Propanol | 4000 | 180 | 560 | $[(i-C_3H_7O)_3Si(CH_2)_3]_2S_2$ | 51.56 / 51.13 | 9.74 / 9.49 | 10.05 / 10.62 | 11.47 / 11.82 |
| $Cl_3Si(CH_2)_2Cl/1981$ | 1900 i-Propanol | 4000 | 480 | 560 | $[(i-C_3H_7O)_3Si(CH_2)_2]_2S_4$ | 44.41 / 44.30 | 8.47 / 8.29 | 9.43 / 9.60 | 21.55 / 21.22 |
| $Cl_3Si(CH_2)_2Cl/1981$ | 1900 i-Propanol | 4000 | 320 | 560 | $[(i-C_3H_7O)_3Si(CH_2)_2]_2S_3$ | 46.93 / 46.38 | 8.95 / 8.75 | 9.98 / 9.90 | 17.08 / 17.79 |
| $Cl_3Si(CH_2)_2Cl/1981$ | 1900 i-Propanol | 4000 | 180 | 560 | $[(i-C_3H_7O)_3Si(CH_2)_2]_2S_2$ | 49.77 / 49.46 | 9.49 / 9.31 | 10.58 / 10.73 | 12.07 / 12.80 |

The process of the invention can comprise, consist essentially of or consist of the steps set forth.

EXAMPLE 1

There were present in a 10 liter three necked flask equipped with stirrer, internal thermometer, reflux condenser and solids supplying apparatus 2120 grams of 3-chloropropyltrichlorosilane and 1450 grams (5% excess) ethyl alcohol were added. The mixture was heated up to the boiling of the alcohol. The hydrogen chloride formed was removed while refluxing and passing through dry air (an inert gas, e.g., argon, can also be used). After cooling there were added to the reaction mixture with stirring a further 4000 grams of ethyl alcohol as well as 480 grams of sulfur powder and 560 grams of sodium hydrosulfide. The slow development of hydrogen sulfide was accelerated by heating to the boiling point of the reaction mixture. After ending the reaction the separated sodium chloride was filtered off and the excess alcohol distilled off. There was obtained in practically quantitative yield bis-(3-triethoxysilylpropyl)-tetrasulfide. The compound was characterized by NMR and IR spectra and elemental analysis.

Results of the elemental analysis in weight percent:

| | C | H | Si | S |
|---|---|---|---|---|
| Calculated: | 40.11 | 7.84 | 10.42 | 23.79 |
| Found: | 39.96 | 7.70 | 10.58 | 23.65 |

A further advantage of the process of the invention in comparison to the processes according to the state of the art is the uniformity of the sulfur value obtained of the product of the process to the theoretical if the starting material is hydrogen chloride free ethoxysilane (or other alkoxysilane) (see Example 1), since the stoichiometry of the reaction is better controlled and maintained. For example, in a previously known process as the last production step the chloropropyltrimethoxysilane is reacted with $Na_2S_4$ in alcoholic solution, whereby concentrations of about 120 grams of $Na_2S_4$ per liter of alcohol must be maintained. In contrast, the new process permits a method of operation independent of the concentration of the starting material in alcohol and the industrial expense required in the new process is considerably less than in customary processes.

What is claimed is:

1. A process for the production of a sulfur containing organosilicon compound of the formula (I) Z-Alk-Sx-Alk-Z, where Z is the grouping:

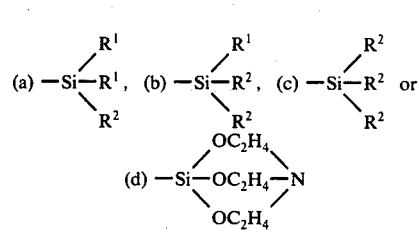

in which $R^1$ is an alkyl group having 1 to 8 carbon atoms, a cycloalkyl group having 5 to 8 carbon atoms, benzyl, phenyl or phenyl substituted with at least one methyl, ethyl or chloro group and $R^2$ is alkoxy of 1 to 8 carbon atoms, methoxyethoxy, cycloalkoxy having 5 to 8 carbon atoms, benzyloxy, phenoxy or phenoxy substituted with at least one methyl, ethyl or chloro group, Alk is a divalent hydrocarbon group having 1 to 10 carbon atoms or such a group interrupted once or twice by —O—, —S— or —NH— and $x$ is a number from 2 to 6 comprising reacting a compound of the formula (II) Y-Alk-Hal, where Y is:

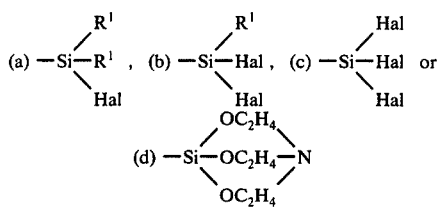

where Hal is fluorine, chlorine, bromine or iodine with, when II is (a), (b) or (c), a compound of the formula $R^3OH$ in which $R^3$ is alkyl of 1 to 8 carbon atoms, methoxyethyl, cycloalkyl having 5 to 8 carbon atoms, benzyl, phenyl or phenyl substituted with at least one methyl, ethyl or chloro group and reacting the resulting product or, when II is (d) reacting II, with a hydrosulfide of the formula III MeSH in which Me is ammonium, an alkali metal atom, an equivalent of an alkaline earth metal or zinc and with sulfur, the amount of sulfur together with the sulfur in MeSH being sufficient to satisfy $x$ in formula I, and removing the ammonium or metal halide.

2. The process of claim 1 wherein the reaction with the MeSH and sulfur is carried out in the presence of an organic solvent.

3. The process of claim 1 where $R^2$ is alkoxy of 1 to 8 carbon atoms, methoxyethoxy, cycloalkoxy having 5 to 8 carbon atoms, phenoxy or benzyloxy and $R^3$ is alkyl of 1 to 8 carbon atoms, methoxyethyl, cycloalkyl having 5 to 8 carbon atoms, phenyl or benzyl.

4. The process of claim 3 wherein the reaction with the MeSH and sulfur is carried out in the presence of an organic solvent and the process includes the step of removing the organic solvent.

5. The process of claim 4 wherein the organic solvent is an alkanol, a cycloalkanol, a phenol or an inert organic solvent.

6. The process of claim 5 wherein the organic solvent is excess of the compound $R^3OH$.

7. The process of claim 3 wherein all of the halogen atoms of Hal having an atomic weight of 9 to 80.

8. The process of claim 7 wherein all of the halogen atoms of Hal are chlorine.

9. The process of claim 8 wherein I is (c) and Y is (c).

10. The process of claim 3 wherein the reaction of II (a), (b) or (c) with $R^3OH$ is carried out at a temperature from 20° C to the boiling point and the reaction with MeSH and sulfur is carried out at 20° C to the boiling point.

11. The process of claim 3 wherein II is (a), (b) or (c).

12. The process of claim 11 wherein the hydrogen halide formed in the first step is removed prior to the reaction with MeSH and sulfur.

13. The process of claim 3 wherein in the step of sulfide formation there is employed sodium, potassium, cesium or ammonium hydrosulfide in powder form and the sulfur is also employed in powder form.

14. The process of claim 13 wherein the reaction is carried out in an inert organic solvent or a compound $R^3OH$ which at least partially dissolves the reactants, the reaction being carried out at a temperature of 20° C to the boiling point of the solvent.

15. The process of claim 14 wherein II is (a), (b) or (c) and the process comprises removing the hydrogen halide formed in the first step of the reaction prior to the reaction with MeSH and sulfur.

16. The process of claim 15 wherein Hal is chlorine.

17. The process of claim 16 wherein II is (c).

18. A process according to claim 11 wherein the hydrosulfide of formula III and the sulfur are reacted with the product resulting from the reaction of the compound of formula II with the compound $R^3OH$ before removing any excess compound $R^3OH$ from the reaction product of the compound of formula II and $R^3OH$.

* * * * *

UNITED STATES PATENT OFFICE
CERTIFICATE OF CORRECTION

Patent No. 4,072,701    Dated February 7, 1978

Inventor(s) Hans-Dieter PLATKA, Rudolf MICHEL

It is certified that error appears in the above-identified patent and that said Letters Patent are hereby corrected as shown below:

At col. 1 line 60 rewrite the formula as

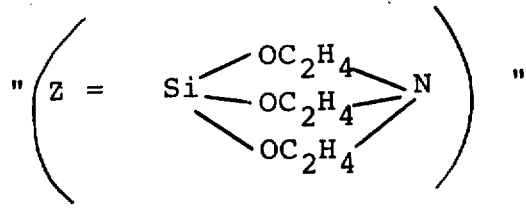

Col. 4 line 5 change "3" to "2"
Col. 4 line 39 change "toly" to "tolyl"
Col. 4 line 58 to col. 5 line 11 rewrite as follows:

$-CH_2-S-CH_2-$; $-CH_2-O-CH_2-$; $-CH_2-NH-CH_2-$; $-CH_2-S-CH_2CH_2-$; $-CH_2-O-CH_2CH_2-$; $-CH_2-NH-CH_2CH_2-$; $-CH_2-S-CH_2CH_2-$; $CH_2CH_2-O-CH_2CH_2-$; $-CH_2CH_2-NH-CH_2CH_2-$; $-CH_2-S-CH_2-S-CH_2-$; $-CH_2-O-CH_2-O-CH_2-$; $-CH_2-NH-CH_2-NH-CH_2-$; $-CH_2-S-CH_2CH_2-S-CH_2-$; $-CH_2-O-CH_2CH_2-O-CH_2-$; $-CH_2-NH-CH_2CH_2-NH-CH_2-$; $-CH_2CH_2-S-CH_2-S-CH_2CH_2-$; $-CH_2CH_2-O-CH_2-O-CH_2CH_2-$; $-CH_2CH_2-NH-CH_2-NH-CH_2CH_2$; $-CH_2CH_2-S-CH_2CH_2-S-CH_2CH_2-$; $-CH_2CH_2-O-CH_2CH_2-O-CH_2CH_2$; $-CH_2CH_2-NH-CH_2CH_2-NH-CH_2CH_2-$; $-(CH_2)_3-S-(CH_2)_3-S-(CH_2)_3-$; $-(CH_2)_3-O-(CH_2)_3-O-(CH_2)_3-$; $-(CH_2)_3-NH-(CH_2)_3-NH-(CH_2)_3-$; $-CH_2CH(CH_3)-O-CH_2CH(CH_3)-O-CH_3CH(CH_3)-$; $-(CH_2)_4-NH-(CH_2)_4-$; $-(CH_2)_4-O(CH_2)_4-$; $-(CH_2)_2CH(CH_3)-S-CH(CH_3)(CH_2)_2-$; $-(CH_2)_5-O(CH_2)_5-$; $-(CH_2)_5-$

UNITED STATES PATENT OFFICE
CERTIFICATE OF CORRECTION

Patent No. 4,072,701                    Dated February 7, 1978

Inventor(s) Hans-Dieter PLATKA, Rudolf MICHEL

It is certified that error appears in the above-identified patent and that said Letters Patent are hereby corrected as shown below:

$S-(CH_2)_5-$; $-(CH_2)_5-NH-(CH_2)_5-$.

Col. 5 last line rewrite the formula

" 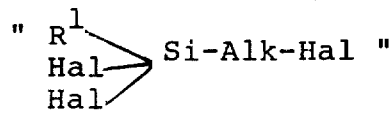 "

Col. 6 line 1 cancel "Alk Hal"
Col. 6 line 29 change "hydrogen sulfide" to "hydrosulfide"

Signed and Sealed this

Twenty-fifth Day of July 1978

[SEAL]

Attest:

RUTH C. MASON
*Attesting Officer*

DONALD W. BANNER
*Commissioner of Patents and Trademarks*